United States Patent [19]

Fridovich et al.

[11] Patent Number: 5,227,405

[45] Date of Patent: * Jul. 13, 1993

[54] SUPEROXIDE DISMUTASE MIMIC

[75] Inventors: Irwin Fridovich, Durham; Douglas J. Darr, Timberlake; Wayne F. Beyer, Bahama, all of N.C.

[73] Assignee: Duke University, Durham, N.C.

[*] Notice: The portion of the term of this patent subsequent to Jun. 29, 2010 has been disclaimed.

[21] Appl. No.: 250,367

[22] Filed: Sep. 28, 1988

Related U.S. Application Data

[63] Continuation-in-part of Ser. No. 32,475, Mar. 31, 1987.

[51] Int. Cl.$^5$ .................. A61K 31/13; A61K 31/16; C07C 233/31

[52] U.S. Cl. ..................... 514/612; 514/616; 564/114; 564/152; 564/153; 435/189; 424/944; 424/DIG. 6

[58] Field of Search ........ 435/189; 424/94.4, DIG. 6; 514/616, 516, 612; 564/153, 114, 152

[56] References Cited

U.S. PATENT DOCUMENTS

| | | | |
|---|---|---|---|
| 3,320,046 | 5/1967 | Siegel | 71/2.4 |
| 4,172,072 | 10/1979 | Ashmead | 260/115 |
| 4,216,143 | 8/1980 | Ashmead | 260/113 |
| 4,346,174 | 8/1982 | Yasuda | 435/189 |
| 4,530,963 | 7/1985 | Devoe et al. | 525/54.1 |
| 4,647,447 | 3/1987 | Gries | 424/9 |
| 4,758,422 | 7/1988 | Quay | 424/9 |

FOREIGN PATENT DOCUMENTS 0196184 10/1986 European Pat. Off. .
0235361 9/1987 European Pat. Off. .

OTHER PUBLICATIONS

Rabinowitch, H. D., et al. (1987) Free Radical Biology & Medicine 3, 125–131.
Archibald, F. (1983) in Oxy Radicals and Their Scavenger Systems–Cohen et al. eds, Elsevier Pub., N.Y., vol. 1, pp. 207–217.
Archibald, F. S. et al. (1982) Arch. Biochem. Biophys. 214(2), 452–463.
Archibald, F. S., et al. (1982) Arch. Biochem. Biophys 215(2), 589–596.
Fridovich, "Natural and Synthetic Defenses Against Oxygen Radicals", ENVIRONS, Dec. 1986, pp. 2–3.
Helvetica Chimica Acta, vol. 46, No. 4, 1963, pp. 1400–1407 (English Translation enclosed).
Bhuyanza, K. C., et al. (1991) Arch. Biochem. Biophys, 288(2), pre-print.
Chemical Abstracts; vol. 68, No. 15, Apr. 8, 1968–67581n.
Chemical Abstracts; vol. 99, No. 20, Nov. 14, 1983–164612w.
Chemical Abstracts; vol. 96, No. 23, Jun. 7, 1982–195506g.
Chemical Abstracts; vol. 95, No. 9, Aug. 31, 1981–76615m.
Epp et al; 1986 Elsevier Science Publishers B.V. (Biomedical Division) Superoxide and Superoxide Dimutase in Chemistry, Biology and Medicine; G. Rotilio, editor.
Yamaguchi et al; FEBS 3451, vol. 197, No. 1,2; Mar. 1986, pp. 249–252.
Koppenol et al; Archives of Biochemistry and Biophysics, vol. 251, No. 2, Dec. 1986, pp. 594–599.
P. Simon; The Lancet, Aug. 27, 1983; pp. 512–513; Desferrioxamine, Ocular Toxicity and Trace Metals.
Plowman, J. E., et al, (1984) J. Inorg. Biochem 20, 183.

*Primary Examiner*—Charles L. Patterson, Jr.
*Attorney, Agent, or Firm*—Cushman, Darby & Cushman

[57] ABSTRACT

The invention relates to a water-soluble complex formed between a chelating agent and manganese and pharmaceutical compositions thereof. The complex is a low molecular weight mimic of superoxide dismutase. The invention further relates to a method of using the complex comprising treating plant and animal cells with an amount of the complex sufficient to reduce or prevent superoxide radical-induced toxicity.

48 Claims, 8 Drawing Sheets

DESFERRIOXAMINE B

GREEN

PINK

SUPEROXIDE DISMUTASE MIMIC

This is a continuation-in-part of application Ser. No. 07/032,475, filed Mar. 31, 1987.

BACKGROUND OF THE INVENTION

1. Technical Field

The invention relates, in general, to a low molecular weight mimic of superoxide dismutase and, in particular, to a desferrioxamine-manganese complex capable of scavenging superoxide radicals.

2. Background Information

The superoxide radical ($O_2^-$) can be generated within living cells during both enzymic and non-enzymic oxidations. Because of the direct reactivity of $O_2^-$, and the reactivity of secondary free radicals that it can generate, $O_2^{31}$ presents a threat to cellular integrity. This threat is met by a family of defensive enzymes that catalyze the conversion of $O_2^-$ to $H_2O_2 + O_2$. These enzymes, superoxide dismutases (SOD), react with $O_2^-$ at a rate that approaches the theoretical diffusion limit and appear to be important for aerobic life. The $H_2O_2$ generated by SOD is disposed of either by catalytic conversion to $O_2$ and $H_2O$ by catalases, or by reduction to water at the expense of thiol, amine or phenolic substrates by peroxidases.

The superoxide radical has been shown to be an important causative factor in the damage resulting from: a) autoxidation; b) oxygen toxicity; c) the oxygen-dependent toxicity of numerous compounds; d) reperfusion injury; e) inflammation; and f) frostbite; and is implicated in the limited viability of transplanted organs and tissues.

The earliest work bearing on the functions of SOD dealt primarily with oxygen toxicity and with the oxygen-dependent toxicities of viologens, quinones and related redox-cycling compounds. These investigations established that $O_2^-$, made within cells, can kill the cells and that SOD provides a defense. It is now known that $O_2^-$ is not only an unwanted and dangerous byproduct of dioxygen metabolism, but is also produced in large quantities by certain specialized cells, seemingly to serve a specific purpose. Neutrophils, and related phagocytic leucocytes, contain a membrane-associated NADPH oxidase that is activated when the cells are stimulated and that specifically reduces dioxygen to $O_2^-$. A defect in this enzyme weakens the microbicidal activity of these leucocytes, leading to chronic granulomatous disease.

The known association of neutrophils with the inflammatory process, and the production of $O_2^-$ by activated neutrophils, suggests a role for $O_2^-$ in the development, and possibly in the deleterious consequences, of inflammation. An enzymic source of $O_2^-$ decreases the viscosity of synovial fluid by depolymerizing hyaluronate and SOD exerts a protective effect. Injecting an enzymic source of $O_2^-$, such as xanthine oxidase, causes a localized inflammation that can be prevented by scavengers of oxygen radicals, such as SOD.

The anti-inflammatory effect of SOD, noted in model inflammations in laboratory animals, is explained in terms of the inhibition of the production of a neutrophil chemotaxin by the reaction of $O_2^-$ with a precursor present in normal human serum. SOD, when injected into the circulation, is rapidly removed by the kidneys, such that the circulation half life of i.v.-injected bovine SOD in the rat is only 7 minutes. This can be markedly increased by coupling the SOD to polyethylene glycol or ficoll, with a corresponding increase in anti-inflammatory effect.

The tissue damage that develops as a consequence of temporary ischemia has classically been attributed to the lack of ATP which develops during the hypoxia imposed during ischemia. Data support the view that this damage actually occurs during reperfusion and is an expression of increased oxygen radical production. SOD protects against this reperfusion injury.

The mechanism which best fits these data depends upon degradation of ATP to hypoxanthine and upon the conversion of xanthine dehydrogenase to xanthine oxidase, during the period of ischemia. Reperfusion then introduces dioxygen, which is reduced to $O_2^-$ by the action of xanthine oxidase on the accumulated hypoxanthine. As expected from this model, allopurinol, which inactivates xanthine oxidase, also protects against reperfusion injury.

The superoxide dismutases are used as pharmacological agents. They are applied to the treatment of inflammatory diseases and are being investigated in the cases of the reperfusion injury associated with skin grafts, organ transplants, frostbite and myocardial infarction. Size, antigenicity and cost, however, mitigate against their widespread usage. Since the enzyme must be isolated from biological sources, it is in limited supply, very expensive and plagued by problems caused by contaminants.

It has long been apparent that low molecular weight mimics of SOD, capable of acting intracellularly, would be useful. Manganese(II), per se, will scavenger $O_2^-$ and, in suitable buffers, will do so catalytically. However, Mn(II) binds avidly to a number of proteins and in so doing loses its activity. Cu(II) is itself a very effective catalyst of the dismutation of $O_2^-$. Since the first SOD to be discovered was a copper protein, copper-complexes have been examined for SOD activity. The problems with free Cu(II) are that it readily forms a hydroxide and that it binds strongly to many macromolecules. For these reasons Cu(II) per se is most active in acid solutions and in the absence of strongly binding ligands. Among the complexes of Cu(II), the SOD-like activity for which have been reported, are: Cu(lys)$_2$ and Cu(gly-his)$_2$, Cu(diisopropylsalicylate)$_2$, Cu(penicillamine), Cu(histidine), Cu(dipeptides) and Cu(gly-his-lys). There are serious problems with all of these copper complexes. Many are, in fact, merely acting as metal buffers, serving to solubilize the Cu(II) and are of insufficient stability to retain activity in the presence of serum albumin. Investigations of Cu(II) complexes have thus far not resulted in the discovery of any biologically useful mimics of SOD.

SUMMARY OF THE INVENTION

It is an object of the invention to provide an inexpensive, synthetic, low molecular weight mimic of SOD.

It is a further object of the invention to provide a scavenger of superoxide radicals that is not inactivated by proteins.

It is another object of the invention to provide a method of using a low molecular weight mimic of SOD to reduce or prevent the toxicity of superoxide radical-induced toxicity.

It is a further object of the invention to provide a pharmaceutical composition containing, as an active ingredient, a stable, low molecular weight mimic of superoxide dismutase.

Further objects and advantages of the present invention will be apparent from the following detailed description thereof.

The invention relates to a low molecular weight mimic of superoxide dismutase comprising a water-soluble complex formed between a chelating agent, for example, desferrioxamine or analogs or derivatives thereof, and manganese. The mimic, designated DF-Mn when it comprises desferrioxamine and manganese, catalyzes the dismutation of $O_2^-$, and retains its activity in the presence of serum albumin and cellular extracts containing protein. It is anticipated that the mimic, and pharmaceutical compositions thereof, will be useful in the following situations: 1) treating inflammation; 2) extending the storage lifetime of organs and tissues intended for transplantation; 3) decreasing damage to the heart suffered as a consequence of infarction; 4) protecting against tissue death and necrosis following any situation entailing temporary cessation of circulation to a tissue or organ; 5) as a radioprotectant; and 6) as an antioxidant applicable to any free radical chain oxidation in which $O_2^-$ serves either as initiator or chain propagator. It is also anticipated that the mimic will be useful in inhibiting autoxidation reactions, thus providing increased shelf life for food products, pharmaceuticals, and stored blood, etc.

DETAILED DESCRIPTION OF THE INVENTION

Figure 1B:
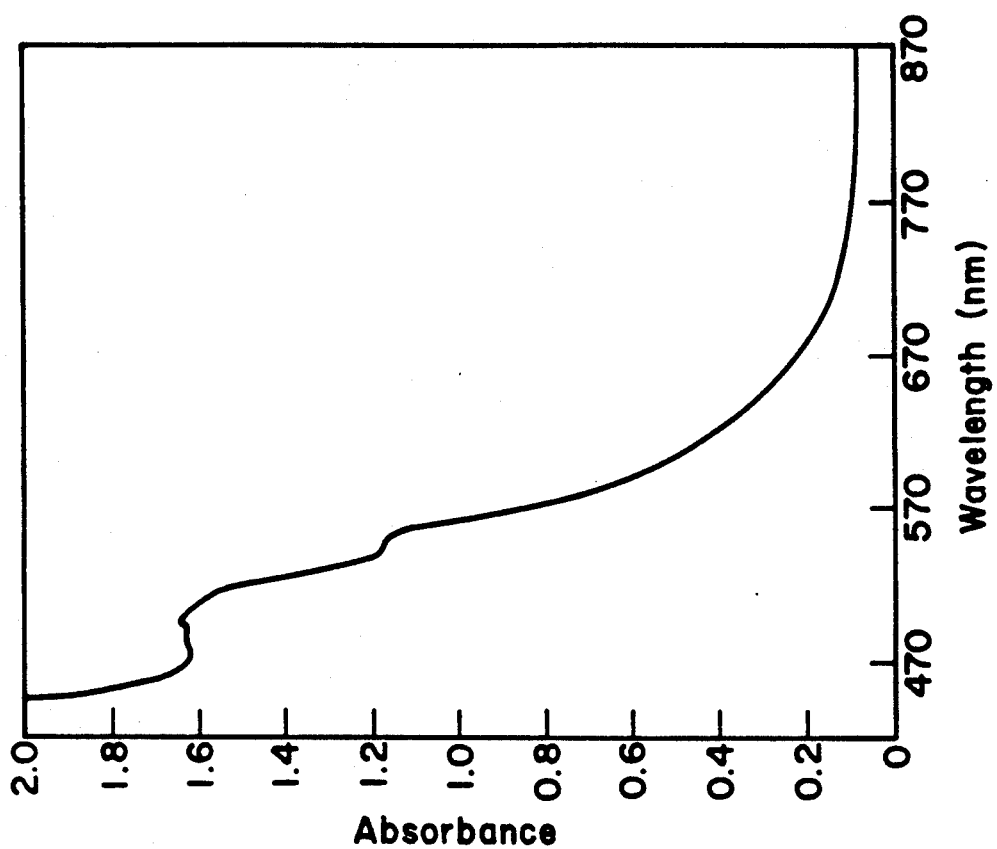
FIG. 1B—Absorption spectra of a pink DF-Mn complex. The pink complex was scanned from 900–500 nm using a Hitachi 100-80 spectrophotometer. The complex was present at about 50 mM in water.

According to the present invention there is provided a low molecular weight mimic of SOD comprising a water-soluble complex formed between a chelating agent and manganese. Chelating agents employed are, advantageously, sideophores, advantageously, of the hydroxamate type, or analogs or derivatives thereof (for review see Neiland, J. B., Inorganic Biochemistry, Eichhorn, G., Ed., Elseiver, Amsterdam, 1973). Suitable hydroxamate-type sideophores include, but are not limited to, schizokinen, hadacidin, rhodotorulic acid, ferrichrome, aspergillic acid and, advantageously, desferrioxamine.

The manganese present in the water-soluble complex has an effective valence of four. The term "effective valence of four" is used to indicate that the manganese present in the complex is that derived either from reacting a chelating agent with a manganese(IV) salt, advantageously, $MnO_2$, or from reacting a chelating agent with a manganese(II) salt, advantageously, $MnCl_2$, which latter reaction is carried out, advantageously, in a neutral oxygenated aqueous solution such that autoxidation of the manganese occurs. It is also contemplated that the above-described water soluble complex comprising a chelating agent and manganese having an effective valence of four, may be derived by reacting a manganese salt, in which salt manganese has a valence of III, V, VI or VII, with a chelating agent under such conditions that the above-described water-soluble complex in which complex manganese has an effective valence of four, is formed. The data presented in Example 1 demonstrate that "an effective valence of four" is in fact equivalent to an actual valence of three.

In one embodiment of the present invention, the complex is that prepared by combining $MnO_2$, advantageously, in approximately 10 percent molar excess, with desferrioxamine, or analogs or derivatives thereof, advantageously, at a concentration of approximately 50 mM, in deionized water or a suitable buffer having a pH of approximately 6 to 8. After stirring until the reaction is complete, that is, advantageously, approximately 12 hours at approximately 25° C. or approximately 6–8 hours at approximately 50° C., residual $MnO_2$ is removed, advantageously, by centrifugation or filtration, leaving a green supernatant solution containing essentially pure DF-Mn.

In another embodiment, the low molecular weight SOD mimic of the instant invention is prepared by dissolving desferrioxamine, or analogs or derivatives thereof, and a reducing agent, for example ascorbic acid, in water, adjusting the pH to approximately 8.5, and adding $MnO_2$. After stirring until the reaction is complete, advantageously about 2 hours, the solution can be clarified, for example, by centrifugation and/or ultrafiltration, leaving a pink solution containing essentially pure DF-Mn.

The complex between a chelating agent and manganese, advantageously DF-Mn, mimics the catalytic activity of native SOD, that is, it is capable of catalyzing the dismutation of $O_2^-$ into $H_2O_2$ and $O_2$, and it is capable of retaining its activity in the presence of serum albumin, total serum or whole bacterial cell extracts. One micromolar DF-Mn exhibits one unit of SOD activity in the xanthine oxidase cytochrome c assay (McCord, J. M. and Fridovich, I. (1969) J. Biol. Chem. 244: 6049–6055). DF-Mn is stable to dilution and to elevated temperatures, that is, of approximately 50° C. An increase in the catalytic activity of DF-Mn, approximately four fold, is achieved by heating the complex, advantageously, at a temperature of approximately 100° C. for approximately 15 minutes. The increase in catalytic activity of DF-Mn achieved by such heating is attributable to a physical change in the complex as evidenced by a change in the color of the solution, that is, the solution which is green prior to heating, becomes gold after the heating process.

The invention contemplates a method of protecting both plant and mammalian cells from the toxicity of superoxide radicals comprising treating the cells with an amount of the above-described water-soluble complex, that is, the complex formed between a chelating agent, advantageously, desferrioxamine or analogs or derivatives thereof, and manganese, sufficient to reduce or prevent superoxide radical-induced toxicity, which complex is capable of catalyzing the dismutation of superoxide radicals and which complex is capable of retaining its activity in the presence of proteins. The complex, advantageously DF-Mn, can be used to protect against the reperfusion injuries encountered during or following: a) organ transplant, b) frostbite; c) angioplasty; d) the administration of streptokinase or tissue plasminogen activator following myocardial infarction. The complex, advantageously DF-Mn, can be used to protect against inflammatory diseases or swelling encountered during or following: a) head injury; b) temporary ischemia to the brain; c) inflammatory joint diseases; and d) gouty attacks. The complex, advantageously DF-Mn, can be used to protect red blood cells in anemia and to prevent rejection of transplanted organs. The complex, advantageously DF-Mn, can be used to inhibit the formation of DNA-breaking clastogenic factor in autoimmune disease.

The complex, advantageously DF-Mn, can be used as a catalytic scavenger of superoxide radicals to provide protection against or treatments for: oxygen toxicity; the oxygen-dependent toxicities of viologens, quinones and related compounds in plants and animals; the very limited storage viability of transplanted hearts, kidneys, skin and other organs and tissues; protection against damage caused by all forms of electromagnetic radiation including visible light, ultraviolet light and ionizing radiation; slowing of the aging process; and protection against the oxygen-dependent toxicities of a variety of redox-active drugs and environmental pollutants.

The invention also contemplates a method of inhibiting damage due to autoxidation of substances resulting in the formation of $O_2^-$ including food products, pharmaceuticals, stored blood, etc. The method comprises adding to food products, pharmaceuticals, stored blood and the like, an amount of the complex, advantageously, DF-Mn, sufficient to inhibit or prevent oxidation damage and thereby to inhibit or prevent the degradation associated with the autoxidation reactions.

It will be clear to one of ordinary skill in the art that the amount of the complex, advantageously DF-Mn, to be used in a particular treatment or to be associated with a particular substance can be determined by one of ordinary skill in the art by routine trials.

The invention further contemplates a pharmaceutical composition comprising, as an active ingredient, the above-described complex, that is, the water-soluble complex formed between a chelating agent, advantageously, desferrioxamine or analogs or derivatives thereof, and manganese, which complex is capable of catalyzing the dismutation of superoxide radicals and which complex is capable of retaining its activity in the presence of proteins, which complex is present in an amount sufficient to reduce or prevent superoxide radical-induced toxicity, together with a pharmaceutically acceptable solid or liquid carrier, diluent or excipient thereof. The composition may take any of the conventional forms for effective administration, e.g., pills, tablets, sterile injectable solutions and the like. When the composition is administered orally, it must be suitably coated, by any of the known techniques, so that it is protected as it passes through the acid environment of the stomach. The composition may also take any of the conventional forms for topical application, e.g, creams, lotions and the like.

The invention is illustrated by way of the following non-limiting examples:

EXAMPLE 1

Preparation and characterization of DF-Mn complexes

Preparation of a DF-Mn complexes

Preparation of a green DF-Mn complex: Desferrioxamine methane sulfate (328 mg) was dissolved in 10 ml of water yielding a 50 mM solution having a pH of approximately 4.0. A 25% molar excess of powdered $MnO_2$ (56 mg) was added. After stirring at 25° C. for 2–4 hours, the unreacted $MnO_2$ was removed by centrifugation and the dark green solution was passed through a 0.22 μ Millex-6 syringe filter and was either used immediately or was lyophilized for storage. When needed, the lyophilized material was dissolved in water.

Preparation of a pink DF-Mn complex: Desferrioxamine methane sulfonate (328 mg) and ascorbic acid (100 mg) were dissolved in 10 ml of water and the pH was adjusted to 8.5 with NaOH. $MnO_2$ (56 mg) was then added and the mixture was stirred for 2 hours and then clarified by centrifugation and ultrafiltration. The resulting pink solution was either used immediately or was lyophilized for storage.

Physiochemical characterization

Figure 1A:
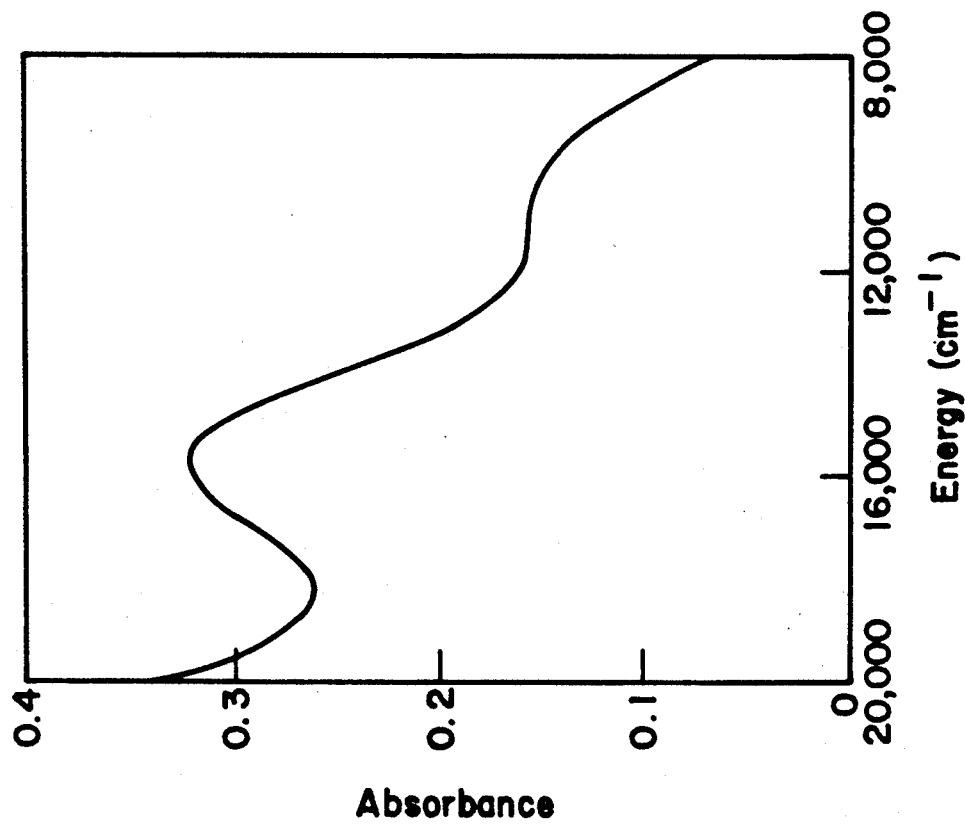
FIG. 1A—Absorption spectra of a green DF-Mn complex. The green complex was scanned from 8000–2000 cm$^{-1}$ using a Perkin Elmer spectrophotometer. The complex was present at about 3 mM in water.

Mn-content and extinction coefficient: The optical spectra (derived using a Hitachi 100/80 or Shimadzu 260 spectrophotometer) of the green and of the pink complexes are shown in FIGS. 1A and 1B, respectively.

The Mn contents of these complexes were determined by atomic absorption spectrophotometry (Perkin Elmer Model 3030 Zeeman effect instrument equipped with an HGA-60 graphite furnace) after dilution with 1% $HNO_3$. Samples of 20 μl were delivered by means of an autosampler onto a L'vov platform in the graphite furnace, along with 50 μg of $Mg(NO_3)_2$, which was added as a matrix modifier. The samples were dried at 140° C. for 60 sec., charred at 1400° C. for 25 sec. and atomized at 2200° C. for 6 sec. Mn absorption was measured at 279.5 nm and peak areas were taken as the measure of the amount of Mn in the samples. A standard curve for Mn(II) was prepared using dilutions from a 1000 μg/ml atomic absorption standard solution from Fisher Scientific Co. The desferrioxamine content of the complexes was based on the assumption that all of the desferrioxamine had been converted to the manganese complexes by the excess of $MnO_2$ which was used. Because of the insolubility of $MnO_2$, it was further assumed that all of the Mn in the test solutions was in the form of the complexes.

The molar ratio of Mn/desferrioxamine in the green complex was 1.13±0.11. This complex exhibited absorption maxima at 640 and 910 nm, with a shoulder at 320 nm. The extinction coefficients were $1.09±0.07×10^2 M^{-1}cm^{-1}$ at 640 nm and $1.57±0.1×10^3 M^{-1}$ at 320 nm. The pink complex yielded a ratio of Mn/desferrioxamine equal to 1.09 ±0.01 and exhibited an absorption maximum at 475 nm, whose Em was $31.2 M^{-1}cm^{-1}$ and a shoulder at 550 nm whose Em was $21.8 M^{-1}cm^{-1}$. The low energy band (910 nm) present in the green complex was noticeably absent in the pink form. It thus appeared that both the green and the pink compounds were 1:1 complexes of manganese with desferrioxamine.

Figure 2A:
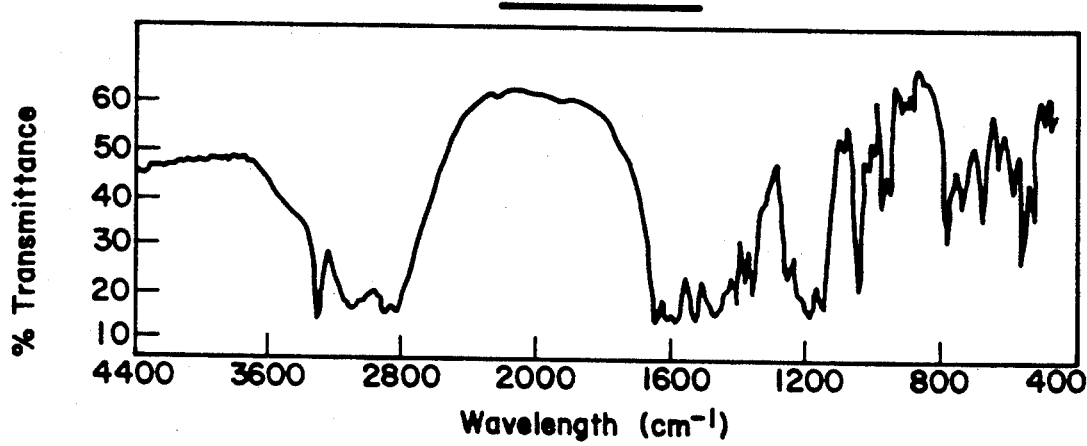
FIG. 2—Infrared spectrum of desferrioxamine (FIG. 2A) and of the DF-Mn green (FIG. 2B) and pink (FIG. 2C) complexes. The lyophilized complexes were pressed into KBr pellets and scanned from 4400–400 cm$^{-1}$ using an Analect IR spectrophotometer.
FIG. 2D is the structure for the linear trihydroxamic acid, desferrioxamine B.
Figure 2B:
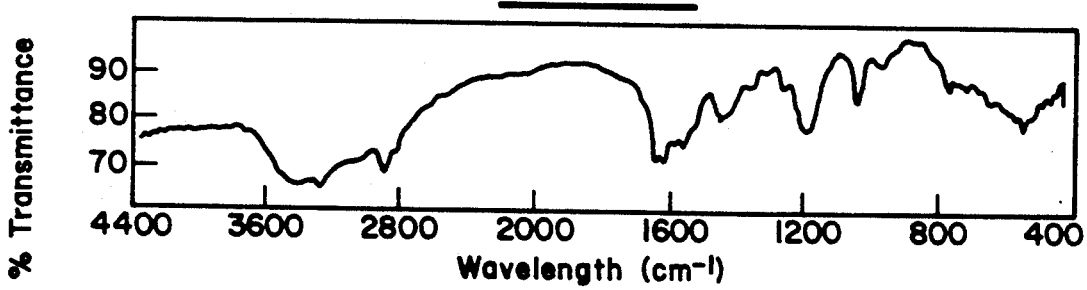
Figure 2C:
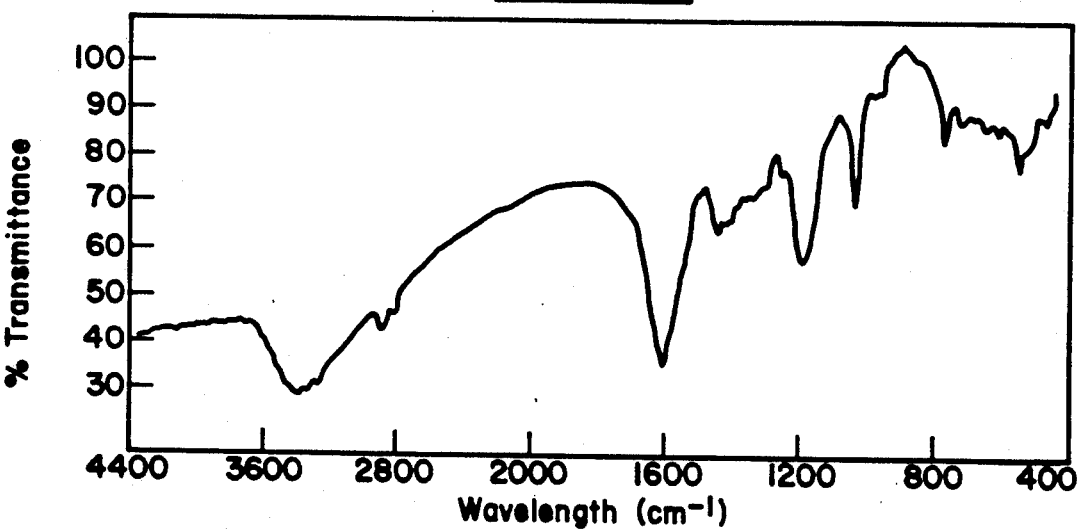
Figure 2D:
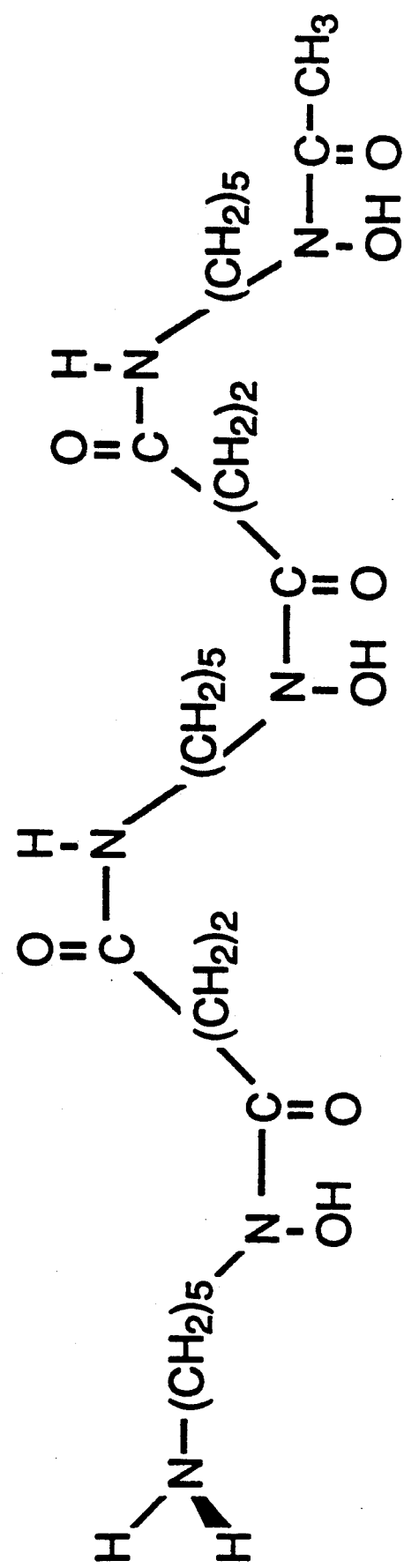

Infrared spectra: Desferrioxamine, the green complex and the pink complex, all in the form of lyophilized powders, were pressed into KBr pellets and their spectra were recorded in the IR region, using an Analect Infrared Spectrophotometer. The spectra shown in FIG. 2 were obtained by averaging 255 scans. Desferrioxamine exhibited a sharp band at 3323 $cm^{-1}$ attributable to the hydroxyl groups on the hydroxamate nitrogen atoms (see the structure in FIG. 2D). Coordination with the manganese caused weakening of the band in the green and pink complexes; in accord with ligation of these hydroxamate oxygen atoms to the metal center. Carboyl stretching bands are seen in the spectrum of desferrioxamine around 1600 $cm^{-1}$ due to the presence of two types of carbonyls i.e., one in the amide and the other in the hydroxamate groups. The green and the pink complexes differ markedly in this region of the spectrum, indicating some difference in the environment of the hydroxamate carbonyl groups.

Figure 3:
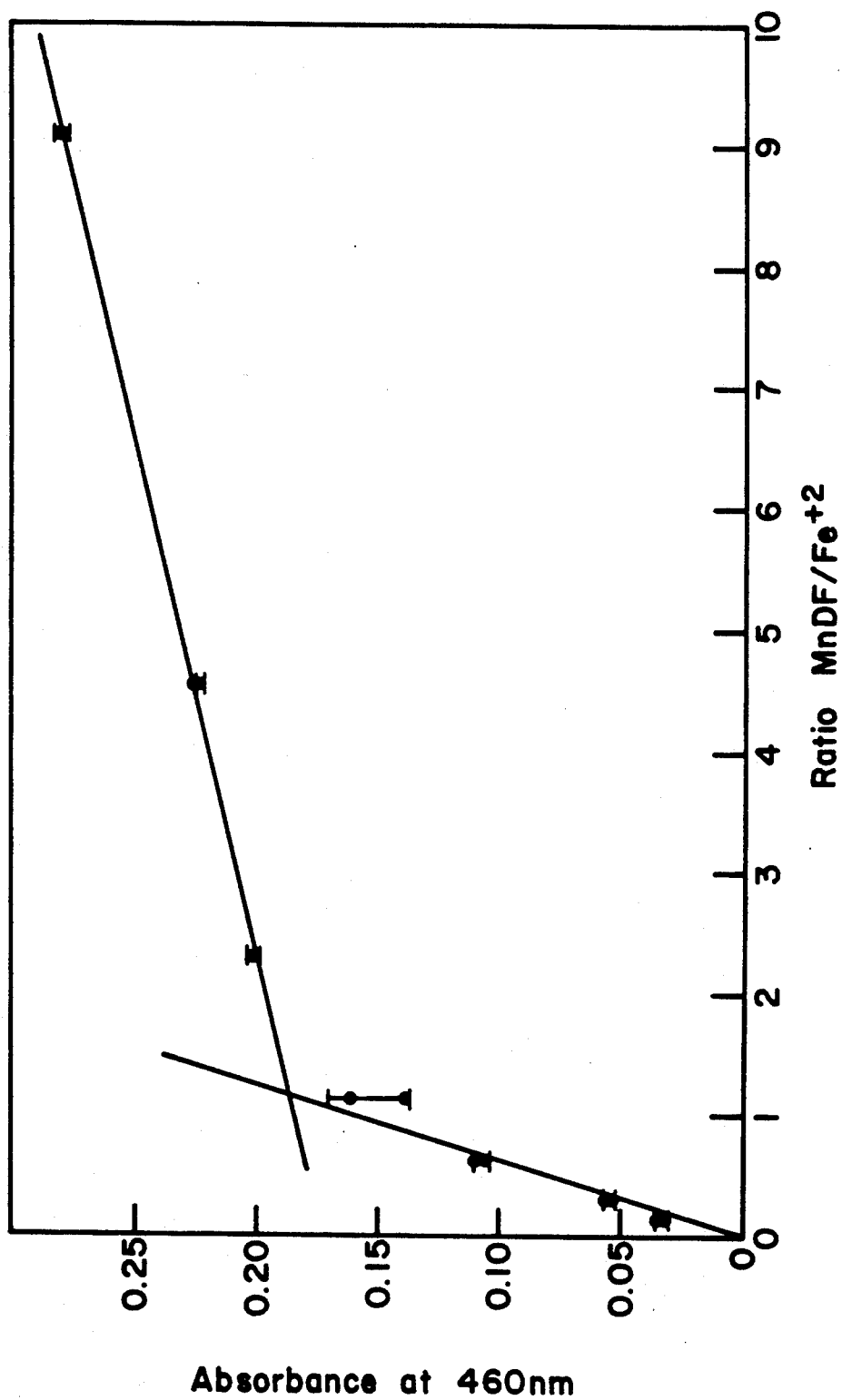
FIG. 3—Oxidation of $Fe^{+2}$ by the green DF-Mn complex in the presence of excess desferrioxamine. The final conditions were 0.28 mM $Fe^{2+}$, 0.35 mM desferrioxamine and 0–1.2 mM green complex The reaction was performed at pH 6.0.

Valence of the manganese in the green and pink complex: When the green complex was mixed with desferrioxamine and $FeSO_4$, at pH 6.0, the yellow-orange color of ferrioxamine developed rapidly; indicating oxidation of the ferrous salt by the green complex, followed by reaction of the resultant Fe (III) with desferrioxamine. The manganese in the green complex is evidently an oxidant towards Fe (II). FIG. 3 presents the results obtained when the ratio of the green complex to the Fe (II) salt was varied at a fixed concentration of the iron salt, and in the presence of excess desferrioxamine. It is clear from the results of this titration that 1.15 moles of the green complex caused the oxidation of one mole of Fe (II) to Fe (III). The modest increase in A460 nm with increasing green complex seen after the equivalence point had been passed is due to the absorbance of the green complex itself at 460 nm. It seems likely from this result that the green complex contains trivalent manganese, that is, that "an effective valence of four" is equivalent to an actual valence of three.

Admixture of equal volumes of 0.25 mM $MnCl_2$ and desferrioxamine followed by adjustment to pH 8.5 resulted in appearance of a green color during 1 hr. of aerobic incubation at 25° C. The rate of color development was augmented by sparging the reaction mixture with 100% dioxygen. On the other hand, exclusion of $O_2$ by sparging with $N_2$ prevented formation of the green complex. If the green complex contained Mn(III) then it would be formed by admixture of $Mn(OH)_3$ with desferrioxamine. $Mn(OH)_3$ was made by a modification of the Winkler method (Sastry et al. *Anal. Chem.* 41:857 (1969)) and it rapidly generated the green complex when stirred with desferrioxamine.

Figure 4:
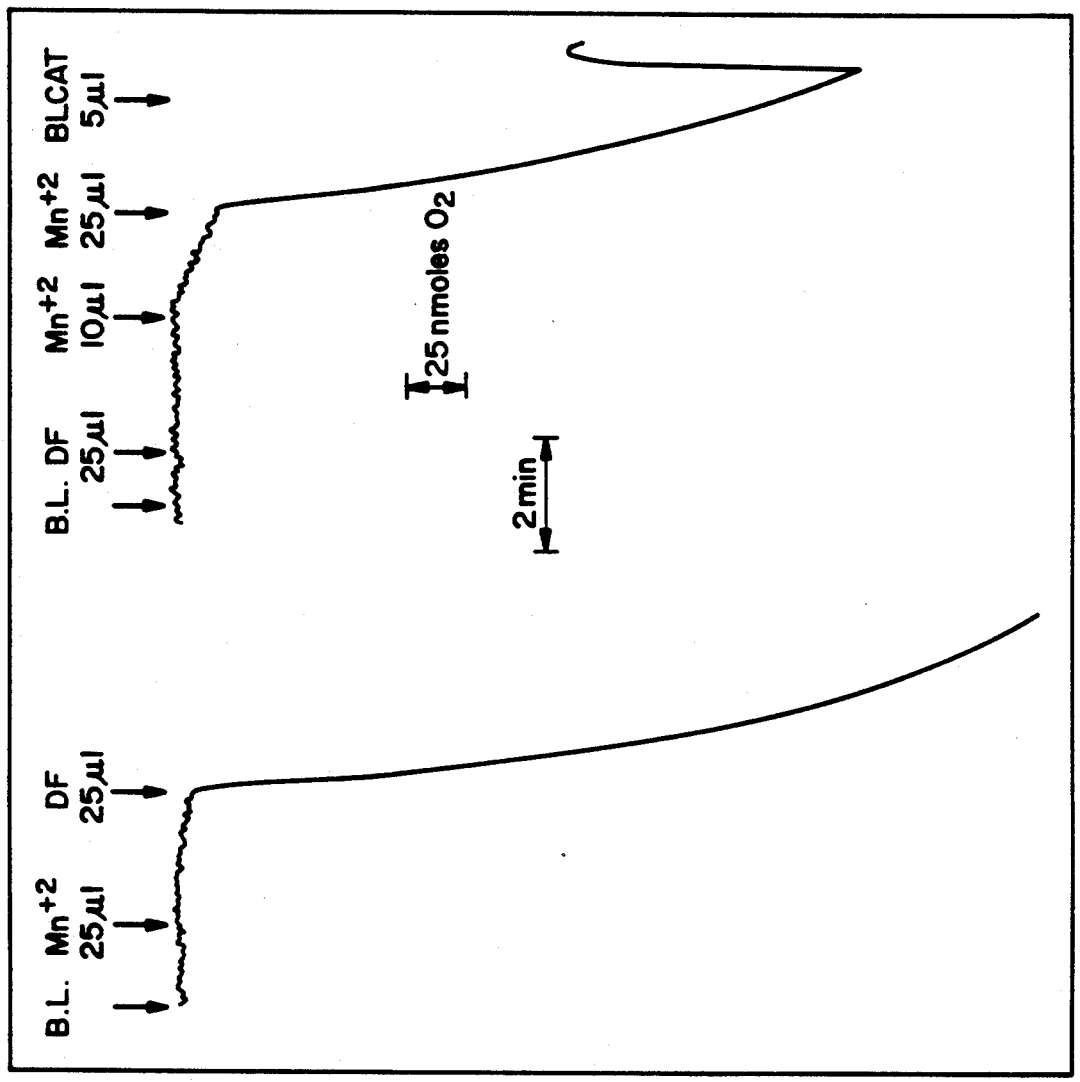
FIG. 4—Stimulation of $O_2$ consumption by $MnCl_2$ and desferrioxamine. The reaction was done in 50 mM CHES (pH 9.15) at 25° C. At the arrows, aliquots of either $MnCl_2$ (100 mM) or desferrioxamine (100 mM) were added and the change in $pO_2$ was recorded using a Clarke-type oxygen electrode. Catalase stock solution was 6.02 mg/ml. The final reaction volume was 20 ml. B.L=base line; DF=desferrioxamine; BLCAT=bovine liver catalase.

Formation of the green complex from desferrioxamine and Mn (II) under aerobic conditions must involve oxidation of Mn (II); favored by the relative stabilization of Mn (III), provided by its much higher affinity for the chelating agent. It follows that addition of desferrioxamine to a salt of Mn (II) should result in consumption of $O_2$. The data in FIG. 4 show that addition of desferrioxamine to Mn (II), or of Mn (II) to desferrioxamine, at pH 9.15, resulted in rapid consumption of $O_2$. Since subsequent addition of catalase caused a return of approximately half of the $O_2$ consumed, it follows that $H_2O_2$ was accumulating in the reaction mixtures.

The foregoing data are consistent with the view that the green complex contains Mn (III). In that case, formation of the complex from $MnO_2$ plus desferrioxamine must involve reduction of the Mn (IV) by the desferrioxamine. $O_2$ is not involved in this process, which was seen to proceed anaerobically. Hydroxamates are reductants and it is likely that one of the hydroxamate groups of the desferrioxamine served as the reductant for the Mn (IV). Provision of an alternate reductant, such as ascorbate, might save the hydroxamate group and yield a complex in which all three hydroxamates remain intact. Such, presumably, is the nature of the pink complex.

Effects of EDTA on the green and the pink complexes: EDTA caused an immediate bleaching of the green complex; which was complete when the EDTA was added in stoichiometric, or greater, amounts. When EDTA was added to a relatively concentrated solution of the complex (10 mM), a faint pink color developed and then disappeared in less than 5 min. at 25° C. It seems likely that EDTA can rapidly displace the desferrioxamine from the metal, yielding the faintly pink Mn (III) EDTA which is unstable because the EDTA then acts as reductant towards the trivalent manganese.

The pink complex, in contrast, was not bleached by EDTA, even when the EDTA was added in 20 fold molar excess over the complex. The pink complex is thus stable to EDTA. Nevertheless the abilities of both the pink and the green complexes to catalyze the dismulation of $O_2$ were eliminated by EDTA. This may be explained by a valence change at the Mn center, during the catalytic cycle, which allows EDTA to displace desferrioxamine from the pink complex.

Figure 5:
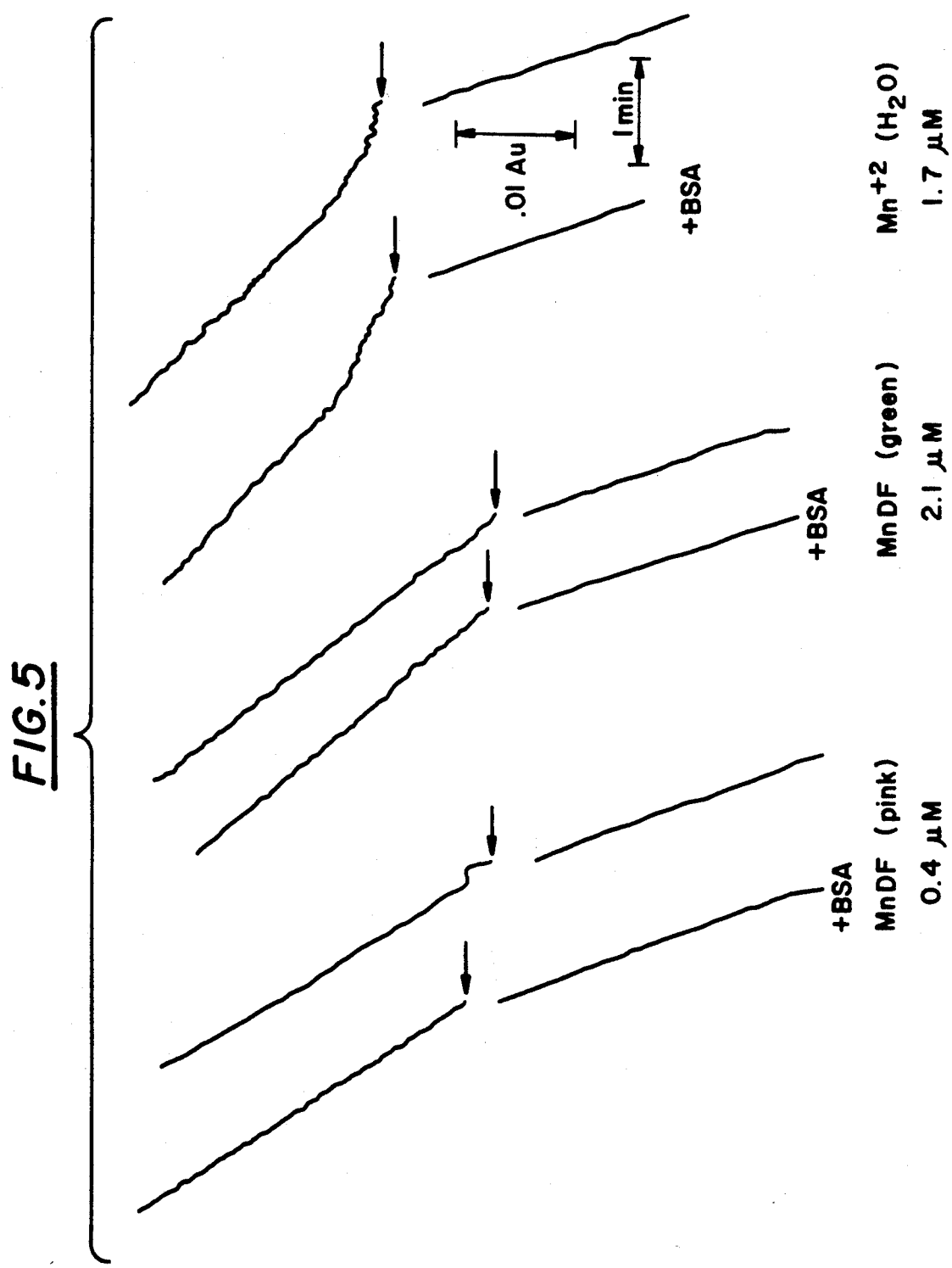
FIG. 5—SOD mimic activity of free and complexed manganese. The reactions contained 50 mM $KP_i$ (pH 7.8) buffer, 10 μM cytochrome $c^{+3}$ 50 μM xanthine and about 8–10 nM xanthine oxidase in a final volume of 3.0 ml. The absorbance change at 550 nm due to the reduction of cytochrome $c^{+3}$ by $O_2$ was recorded in the absence (lower curves) and presence (upper curves) of the indicated manganese species MnDF=Mn-desferrioxamine complex.
Figure 6A:
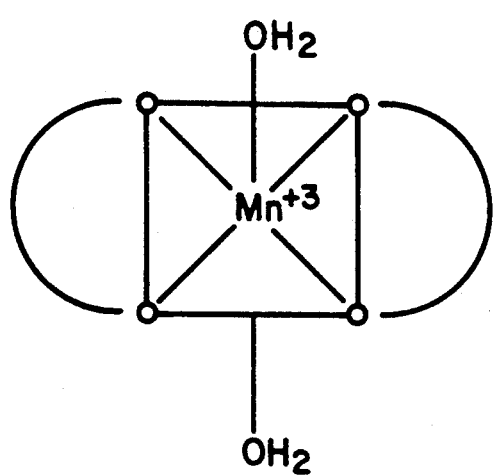
In FIG. 6A, the oxidized hydroxamate has been omitted for clarity.
Figure 6B:
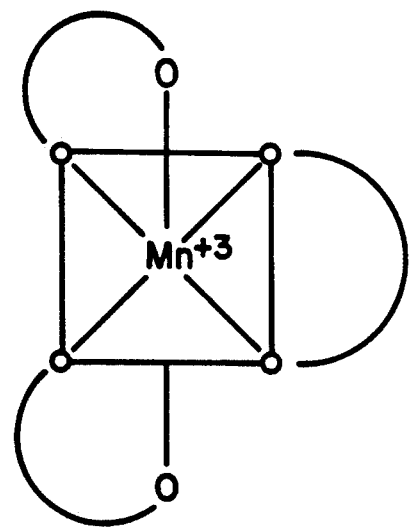
FIG. 6—Proposed structures for the pink and green complexes resulting from the reaction between $MnO_2$ and desferrioxamine prepared in the absence of ascorbate (FIG. 6A) and in the presence of ascorbate (FIG. 6B). In both FIGS. 6A and 6B, the polypeptide backbone is omitted for clarity (see FIG. 6C).
Figure 6C:
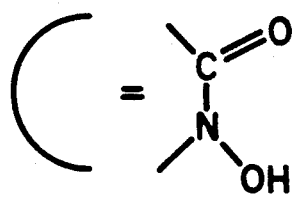

SOD-like activities of the complexes: The green complex has previously been reported to mimic the activity of SOD (Darr et al. *Arch Biochem. Biophys.* 258:351 (1987)). FIG. 5 compares the abilities of the green and the pink complexes, with that of Mn (II), to inhibit the reduction of cytochrome c by an enzymic source of $O_2^-$. Mn (II) can be distinguished because its inhibition was biphasic; while that due to the complexes was not. Thus, addition of Mn (II) caused an immediate and strong inhibition; which then diminished until a lesser, but stable, inhibition was achieved. In contrast, the green and the pink complexes immediately imposed a degree of inhibition which was stable with time. In the case of Mn (II) the first reaction of the catalytic cycle thus appears to be more rapid than the subsequent reactions; whereas in the cases of the complexes, the rate of first step of the catalytic cycle is equal to, or less than, subsequent steps. When compared on the basis of stable inhibitions the SOD-like activities of Mn (II), pink, and green complexes on a per manganese basis fall in the ratio 1.0:1.7:0.3.

EXAMPLE 2

Catalytic activity of DF-Mn in the presence of protein

Using the cytochrome c reduction assay (McCord, J. M. and Fridovich, I. (1969) J. Biol. Chem. 244; 6049-6055) in the presence of increasing amounts of serum albumin, total serum or whole bacterial cell extracts, a 1 µM solution of DF-Mn (green complex) exhibited one unit (defined in above reference) of SOD activity.

EXAMPLE 3

Catalytic activity of rhodotorulic acid and manganese

A complex was formed by reacting rhodotorulic acid with $MnCl_2$ in a ratio of 1:1 in a neutral, oxygenated aqueous solution. The pH was adjusted to 8. A 1 µM solution of the complex had approximately 1 unit of SOD activity as assayed using the cytochrome c reduction assay.

Rhodotorulic acid was also reacted with $MnO_2$. A colored complex was formed.

EXAMPLE 4

Protection of mammalian cells against oxygen toxicity by DF-Mn (green complex)

Chinese hamster ovary cells were exposed to paraquat (200 µM), a compound known to form $O_2^-$ intracellularly. After an eight-hour exposure, 50 to 70% cell death was observed. Pretreatment with 20 µM DF-Mn reduced cell death by 70±9% (mean±SD; N=8 experiments). Desferrioxamine, manganese (chloride or dioxide), or EDTA-Mn alone at 20 µM gave little or no protection. Native Cu-Zn SOD was also less effective, presumably because it could not enter the cells. Copper-DIPS gave approximately 30% protection when present at levels exhibiting 10 times the "SOD" activity of DF-Mn (green complex). The data indicate that DF-Mn can enter mammalian cells and afford protection against paraquat-mediated damage.

EXAMPLE 5

Protection by DF-Mn (green complex) against damage to mammalian lenses by superoxide radicals generated during cyclic, oxidation-reduction of redox compounds Fresh lenses of rabbits were incubated in Krebs-Ringer medium with Hepes buffer (pH 7.4) and 5 mM glucose at 37° C. for 3 hours. Malondialdehyde, a marker of lens damage, was 1.16±0.12 nmole/g wet weight in control lenses. This increased 6-8 fold (p<0.001) in the presence of 1 mM paraquat, diquat, plumbagin or juglone. In such lenses, reduced glutathione (GSH) was decreased 30-55% as compared to 8.74±0.12 µmole/g wet weight in lenses incubated in the absence of these compounds. Under identical experimental conditions, other protein-SH of lenses were not significantly altered. AMM, a liposomal superoxide dismutase (Michelson, A. M., Puget, K., Durosan, P. (1981), Molec. Physiol. 1:85-96) or 1 mM DF-Mn (green complex) significantly prevented these changes to the lens. The involvement of oxygen radicals in the toxicity of these redox compounds is evidenced by the fact that lenticular damage was potentiated in the presence of 100% $O_2$ as gas phase and negligible in 100% $N_2$.

EXAMPLE 6

Protection by DF-Mn (green complex) of the green alga, Dunaliella salina, from the effects of paraquat

Experimental Conditions

Culture Conditions: Dunaliella salina was cultivated phototrophically in mineral medium (J.Phycol.18:5-29-537 (1982)) with modification. The medium contained 0.3 mM $CaCl_2$; 2 µM $FeCl_3$; 20 µM EDTA; 0.1 mM $KH_2PO_4$; 5.0 mM $KNO_3$; 5 mM $MgSO_4$; 50 mM $NaHCO_3$; and 1.67 M NaCl. $FeCl_3$ and EDTA were premixed prior to being added to the medium. The pH of the medium was maintained at 6.8. Cultures were inoculated and allowed to grow for 2-3 days, aliquots were then placed on a gyrating platform for the experimental treatments. Illumination was provided by natural daylight supplemented by incandescent bulbs.

Assays: Algal cells were collected by centrifugation and chlorophyll was extracted by resuspension in N,N-dimethylformamide for 24 hours at 4° C. with occasional agitation. After clarification by centrifugation, the dissolved chlorophyll was estimated from measurements of absorbance at 664 and 647 nm (Plant Physiol. 65:478-479 (1980). Plant Physiol. 69:1376-1381 (1980)). Algal cultures, intended for assays of protein and of enzymic activities, were harvested by centrifugation during log phase and were washed by gentle resuspension in 50 mM potassium phosphate, 0.1 mM EDTA, pH 7.8, followed by centrifugation. The cells were resuspended in phosphate-EDTA buffer and were lysed by being passed through a French Pressure Cell. Lysates were clarified and the resultant soluble extracts assayed for protein, and for SOD (J. Biol. Chem. 244:6049-6055 (1969)) and catalase (J. Biol. Chem. 195:133-140 (1952)) activities.

Paraquat and electrophoresis: When the effects of paraquat were being investigated, the compound was added to cultures which had been growing for 48 hours and were still in log phase, the incubation was continued for 18 hours. The cells were assayed for chlorophyll content or for protein and enzymic activities as described above. Electrophoresis was performed on 7% polyacrylamide gels and duplicate electropherograms were stained for catalase (Anal. Biochem. 140:532-537 (1984)) or for SOD activities (Anal. Biochem. 44:276-278 (1971)).

Experiment

Figure 7:
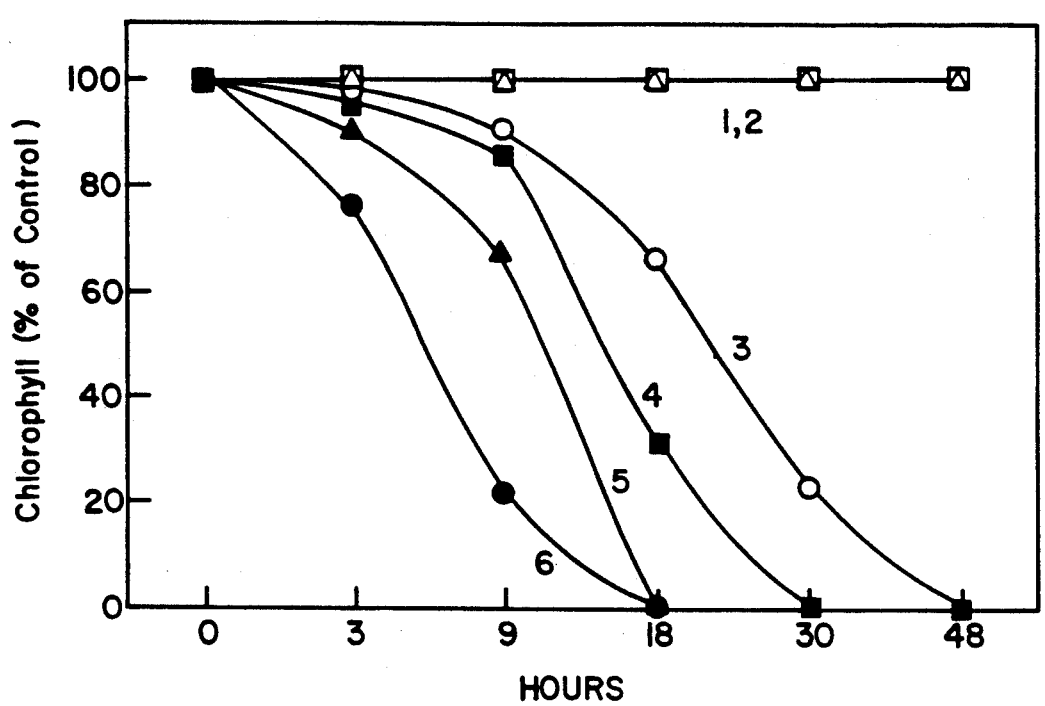
FIG. 7—Bleaching of chlorophyll in *D.salina* by paraquat.
Figure 8:
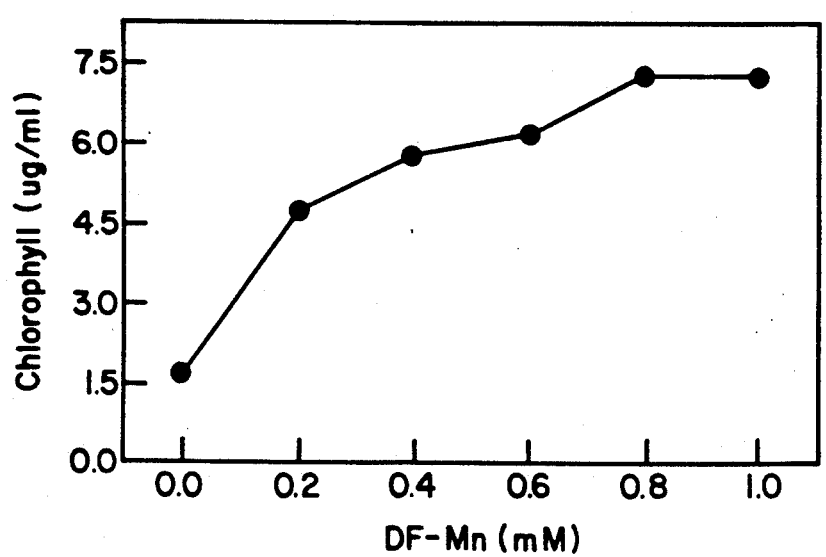
FIG. 8—DF-Mn protection against paraquat.

Illuminated log phase cultures of D. salina were bleached when exposed to paraquat at, or exceeding, 250 µM. This progressive bleaching, shown in FIG. 7 (line 1=0.05 mM, line 2=0.10 mM, line 3=0.25 mM, line 4=0.5 mM, line 5=1.0 mM, line 6=1.5 mM), was accompanied by loss of motility observed under light microscope. DF-Mn (green complex), when present in the culture medium, protected against the bleaching effect of paraquat in a dose-dependent manner (FIG. 8). The protective effect of DF-Mn was not due to masking of incident light since at 634 nm the ratio of the absorbance of DF-Mn to that of chlorophyll was 0.1/0.731; while at 433 nm the ratio was 0.24/1.45.

The results in Table I indicate that DF-Mn exerts its protective effect very soon after being added to the medium. Since neither SOD nor catalase, added to the suspending medium, protected against the toxicity of paraquat (Tables II and III), it is apparent that scavenging of $O_2^-$ or of $H_2O_2$ in the medium is not an effective means of protection. Washing *D. salina* exposed to DF-Mn restores sensitivity towards paraquat, indicating that DF-Mn, having entered the cells, readily diffused out.

The protective effect of DF-MN is due to the complex itself rather than to the products of its dissociation. This is evidenced by the fact that desferrioxamine alone caused a progressive bleaching of the cultures in the absence of paraquat. Mn(II) or Mn(III)-pyrophosphate, failed to protect *D. salina* against the deleterious effects of paraquat. $MnO_2$ alone is essentially insoluble in water and had no effect on the bleaching of *D. salina* by paraquat.

The foregoing invention has been described in some detail by way of examples for purposes of clarity and understanding. It will be obvious to those skilled in the art from a reading of the disclosure that it is contemplated that the compound and composition thereof described herein will be used to inhibit the deleterious effects of superoxide radicals both in agricultural and clinical settings. Various combinations in form and detail can be made without departing from the scope of the invention.

The entire contents of all published articles cited herein are hereby incorporated by reference.

TABLE I

Effect of DF—Mn on the Bleaching of D. salina by Paraquat

| Treatment | Chlorophyll (μg/ml) | | Chlorophyll/Dry Weight (μg/mg) |
| --- | --- | --- | --- |
| | chl a | Total | Total |
| Control | 12.7 ± 0.6 | 17.1 ± 0.9 | 3.4 ± 0.4 |
| Paraquat[a] | 0.0 | 0.0 | 0.0 |
| DF—Mn[b] | 13 ± 1 | 17 ± 1.1 | 3.2 ± 0.3 |
| DF—Mn 30 min prior to paraquat | 6.6 ± 0.9 | 9.3 ± 1.3 | 1.9 ± 0.3 |
| DF—Mn 30 min following paraquat | 6.2 ± 0.8 | 9.0 ± 1.2 | 2.0 ± 0.3 |

[a]Paraquat was added to a final concentration of 1.0 mM.
[b]DF—Mn (green complex) was added to a final concentration of 1.0 mM.

TABLE II

Effect of DF—Mn and of SOD on the Bleaching of D. salina by Paraquat

| Treatment | Chlorophyll (μg/ml) | | Chlorophyll/Dry Weight (μg/mg) |
| --- | --- | --- | --- |
| | chl a | Total | Total |
| Control | 15.6 ± 1.2 | 20.2 ± 1.6 | 3.6 ± 0.4 |
| Paraquat[a] | 0.0 | 0.0 | 0.0 |
| DF—Mn[b] | 16.3 ± 0.8 | 21.3 ± 1.0 | 3.6 ± 0.4 |
| SOD[c] + paraquat | 0.0 | 0.0 | 0.0 |
| DF—Mn[b] + SOD | 16.6 ± 0.4 | 21.8 ± 0.3 | 4.0 ± 0.3 |
| DF—Mn + paraquat | 7.5 ± 1.1 | 10.8 ± 1.3 | 1.8 ± 0.2 |
| DF—Mn + SOD + paraquat | 8.8 ± 1.3 | 12.1 ± 1.8 | 2.0 ± 0.3 |

[a]Paraquat was added to 1.0 mM.
[b]DF—Mn (green complex) was added to 1.0 mM.
[c]SOD was added to 10 μg/ml.

TABLE III

Effect of DF—Mn and Catalase on Bleaching of D. salina by Paraquat

| Treatment | Chlorophyll (μg/ml) | | Chlorophyll/Dry Weight (μg/mg) |
| --- | --- | --- | --- |
| | chl a | Total | Total |
| Control | 17.2 ± 0.5 | 22.0 ± 0.6 | 4.0 ± 0.2 |
| Paraquat[a] | 0.0 | 0.0 | 0.0 |
| DF—Mn[b] | 16.0 ± 0.9 | 21.4 ± 0.8 | 3.8 ± 0.2 |
| DF—Mn + paraquat | 10.0 ± 0.2 | 13.6 ± 0.4 | 2.4 ± 0.1 |
| Catalase[c] + paraquat | 0.0 | 0.0 | 0.0 |
| DF—Mn + catalase | 18.1 ± 1.8 | 23.5 ± 2.0 | 4.2 ± 0.3 |
| DF—Mn + catalase + paraquat | 9.4 ± 0.9 | 13.0 ± 1.0 | 2.3 ± 0.2 |

[a]Paraquat was added to 1.0 mM.
[b]DF—Mn (green complex) was added to 1.0 mM.
[c]Catalase was added to 10 μg/ml.

What is claimed is:

1. A low molecular weight mimic of superoxide dismutase activity comprising a water solube complex formed between a chelating agent and manganese, wherein said chelating agent is a hydroxamate-type siderophore, or analog or derivative thereof capable of forming said complex.

2. A mimic of superoxide dismutase activity according to claim 1 wherein said manganese has an actual valence of three.

3. A mimic of superoxide dismutase activity according to claim 1 wherein said chelating agent is desferrioxamine or analog or derivative thereof capable of forming said complex.

4. A mimic of superoxide dismutase activity according to claim 1 in essentially pure form.

5. A pharmaceutical composition comprising, as an active ingredient, a water-soluble complex formed between a chelating agent and manganese, wherein said chelating agent is a hydroxamate-type siderophore, or analog or derivative thereof capable of forming said complex, which complex is present in an amount sufficient to reduce or prevent superoxide radical-induced toxicity, together with a pharmaceutically acceptable carrier.

6. A pharmaceutical composition according to claim 5 wherein said composition is in the form of a cream or a lotion for topical application.

7. A pharmaceutical composition according to claim 5 wherein said composition is in the form of a tablet, capsule or sterile injectible solution.

8. A pharmaceutical composition according to claim 5 wherein said chelating agent is desferrioxzamine or analog or derivative thereof capable of forming said complex.

9. A pharmaceutical compositon according to claim 5 wherein said manganese has an actual valence of three.

10. A low molecular mimic of superoxide dismutase produced by a method comprising the steps of:
a) combining a manganese (IV) salt with a chelating agent in water or an aqueous buffer, wherein said chelating agent is a hydroxamate-type siderophore, or analog or derivative thereof capable of complexing with manganese;
b) stirring said combination until reaction between said chelating agent and manganese is complete; and
c) removing residual manganese salt from a resulting solution.

11. A mimic of superoxide dismutase activity produced by the method according to claim 10 further comprising the step of heating said resulting solution at approximately 100° C. for approximately 15 minutes.

12. A low molecular weight mimic of superoxide dismutase activity produced by a method comprising the steps of:
   a) combinting a manganese(II) salt with a chelating agent in a neutral oxygenated aqueous solution, wherein said chelating agent is a hydroxamate-type siderophore, or analog or derivative thereof capable of complexing with manganese;
   b) stirring said combination until reaction between said chelating agent and manganese is complete; and
   c) removing any residual manganese salt from a resulting solution.

13. A mimic of superoxide dismutase activity produced by a method comprising the steps of:
   a) combing a manganese salt, in which salt manganese has a valence of III, V, VI or VII, with a chelating agent under such conditions that manganese achieves an actual valence of three, wherein said chelating agent is a hydroxamate-type siderophore, or analog or derivative thereof capable of complexing with manganese;
   b) stirring said combination until reaction between said chelating agent and said manganese is complete; and
   c) removing any residual manganese salt from a resulting solution.

14. A low molecular weight mimic of superoxide dismutase activity produced by a method comprising the steps of:
   a) combining a hydroxamate-type siderophore chelating agent and a reducing agent in an aqueous solution and adjusting the pH to about 8.5;
   b) adding to said solution of step (a) a manganese (IV) salt;
   c) allowing said chelating agent to chelate the manganese of said manganese (IV) salt; and
   d) removing residual manganese salt from a solution resulting from step (c) above.

15. The low molecular weight mimic of superoxide dismutase activity according to claim 14 wherein said reducing agent is ascorbic acid, or a salt thereof.

16. The low molecular weight mimic of superoxide dismutase activity according to claim 14 wherein said chelating agent is desferrioxamine.

17. The low molecular weight mimic of superoxide dismutase activity according to claim 14 wherein said manganese (IV) salt is $MnO_2$.

18. A mimic of superoxide dismutase activity produced by the method according to claim 10, wherein said aqueous buffer has a pH of about 6 to 8.

19. A method of protecting cells from the toxicity of superoxide radicals comprising treating said cells with an amount of a water-soluble complex formed between a hydroxamate-type siderophore chelating agent, or analog or derivative thereof capable of complexing with manganese, and manganese sufficient to reduce or prevent superoxide radical-induced toxicity, which complex is produced by a method comprising the steps of:
   a) combining said hydroxamate-type siderophore chelating agent, or analog or derivative thereof, and a reducing agent in an aqueous solution and adjusting the pH to about 8.5;
   b) adding to said solution of step (a) a manganese (IV) salt;
   c) allowing said chelating agent to chelate the manganese of said manganese (IV) salt; and
   d) removing any residual manganese salt from soltuion resulting from step (c) above.

20. The method according to claim 19 wherein said cells are mammalian cells.

21. The method according to claim 19 wherein said cells are plant cells.

22. The method according to claim 19 wherein said superoxide-radicals are the result of a reperfusion injury.

23. The method according to claim 19 wherein said superoxide-radicals are the result of an inflammatory disease.

24. The method according to claim 19 wherein said reducing agent is ascorbic acid, or a salt thereof.

25. The method according to claim 19 wherein said manganese (IV) salt is $MnO_2$.

26. The method according to claim 19 wherein said hydroxamate type siderophore chelating agent is desferrioxamine or analog or derivative thereof capable of forming said complex.

27. A method of inhibiting damage due to auto-oxidation of a substance with the subsequent formation of $O_2$ comprising adding to said substance an amount of a water-soluble complex formed between a hydroxamate-type siderophore chelating agent, or analog or derivative thereof capable of complexing with manganese, and manganese sufficient to reduce or prevent oxidation damage, which complex is produced by a method comprising the steps of:
   a) combining said hydroxamate-type siderophore chelating agent, or analog or derivative thereof, and a reducing agent in an aqueous solution and adjusting the pH to about 8.5;
   b) adding to said solution of step (a) a manganese (IV) salt;
   c) allowing said chelating agent to chelate the manganese of said manganese (IV) salt; and
   d) removing any residual mangese salt from a solution resulting from step (c) above.

28. The method according to claim 27 wherein said reducing agent is ascorbic acid, or a salt thereof.

29. The method according to claim 27 wherein said manganese (IV) salt is $MnO_2$.

30. The method according to claim 27 wherein said hydroxamate-type siderophore is desferrioxamine, or analog or derivative thereof capable of forming said complex.

31. A pharmaceutical composition comprising, as an active ingredient, said low molecular weight mimic according to claim 14 which mimic is present in an amount sufficient to reduce or prevent superoxide radical induced toxicity, together with a pharmaceutically acceptable carrier.

32. A pharmaceutical composition according to claim 31, wherein said reducing agent is ascorbic acid, or a salt thereof.

33. A pharmaceutical composition according to claim 31, wherein said chelating agent is desferrioxamine.

34. The pharmaceutical composition according to claim 31 wherein said composition is in the form of a cream or a lotion suitable for topical application.

35. The pharmaceutical composition according to claim 31 wherein said composition is in the form of a tablet, capsule or sterile injectable solution.

36. The mimic of superoxide dismutase activity according to claim 13 wherein said manganese of said manganese salt has a valence of III.

37. A mimic of superoxide dismutase activity comprising an atom of manganese having an actual valence of 3 complexed with three hydroxamate groups.

38. The mimic of superoxide dismutase activity according to claiim 37 wherein said hydroxamate groups are derived from a single molecule of desferrioxamine.

39. A pharmaceutical composition comprising as an active ingredient said mimic according to claim 37, which mimic is present in an amount sufficient to reduce or prevent superoxide radical induced toxicity, together with a pharmaceutically acceptable carrier.

40. A pharmaceutical composition according to claim 39 wherein said hydroxamate groups are derived from a single molecule of desferrioxamine.

41. A pharmaceutical composition according to claim 39 wherein said composition is in the form of a cream or a lotion suitable for topical application.

42. A pharmaceutical composition according to claim 39 wherein said composition is in the form of a tablet, capsule or sterile injectable solution.

43. A complex of a desferrioxamine and manganese.

44. The complex according to claim 43, wherein the desferrioxamine is a trihydroxamic acid.

45. The complex according to claim 43, wherein the desferrioxamine is of the formula,

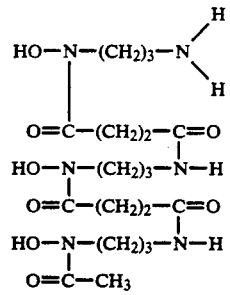

46. A stable aqueous solution of a complex of a desferrioxamine and manganese, containing alkali in amount sufficient to bring the pH to about 6.

47. The solution according to claim 46, wherein the desferrioxamine is a trihydroxamic acid.

48. The solution according to claim 47, wherein the desferrioxamine is of the formula

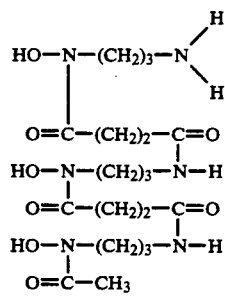

* * * * *